(12) United States Patent
Plank et al.

(10) Patent No.: US 8,113,831 B2
(45) Date of Patent: Feb. 14, 2012

(54) HAND-HELD LIGHT CURING DEVICE

(75) Inventors: Wolfgang Plank, Rankweil (AT); Bruno Senn, Buchs (CH)

(73) Assignee: Ivoclar Vivadent AG, Schaan (LI)

( * ) Notice: Subject to any disclaimer, the term of this patent is extended or adjusted under 35 U.S.C. 154(b) by 349 days.

(21) Appl. No.: 11/823,953

(22) Filed: Jun. 29, 2007

(65) Prior Publication Data

US 2008/0026339 A1  Jan. 31, 2008

Related U.S. Application Data

(60) Provisional application No. 60/880,632, filed on Jan. 16, 2007.

(30) Foreign Application Priority Data

Jul. 31, 2006  (DE) .................. 10 2006 035 658

(51) Int. Cl.
*A61C 3/00* (2006.01)
(52) U.S. Cl. .................................... 433/29
(58) Field of Classification Search .............. 433/29; 320/114, 115; 362/276, 394, 395, 802
See application file for complete search history.

(56) References Cited

U.S. PATENT DOCUMENTS

| | | | |
|---|---|---|---|
| 5,521,392 A * | 5/1996 | Kennedy et al. | 250/492.1 |
| 6,325,791 B1 | 12/2001 | Shimoji | |
| 6,602,074 B1 | 8/2003 | Suh et al. | |
| 6,633,120 B2 | 10/2003 | Salam | |
| 6,798,169 B2 * | 9/2004 | Stratmann et al. | 320/114 |
| 7,049,790 B2 * | 5/2006 | Pfenniger et al. | 320/114 |
| 2002/0177099 A1 | 11/2002 | Cao | |
| 2004/0214138 A1 * | 10/2004 | Senn et al. | 433/141 |
| 2006/0062022 A1 | 3/2006 | Foong | |

FOREIGN PATENT DOCUMENTS

| | | |
|---|---|---|
| DE | 2 361 531 | 6/1974 |
| DE | 8219588 U1 | 2/1985 |
| DE | 101 14 656 A1 | 12/2001 |
| DE | 103 19 010 A1 | 11/2004 |
| DE | 20 2005 011 804 U | 11/2005 |
| EP | 1 260 193 A2 | 11/2002 |
| WO | WO 2006/054236 A2 | 5/2006 |

* cited by examiner

*Primary Examiner* — Cris L Rodriguez
*Assistant Examiner* — Eric Rosen
(74) *Attorney, Agent, or Firm* — John C. Thompson; Sandra J. Thompson; Ann M. Knab

(57) ABSTRACT

The present Invention relates to a hand-held light curing device (10), in particular for the dental sector, with a base station (30) or a rest, on which the light curing device (10) having a light source (10) is supported. A sensor (40) is fitted on the base station (30) or the rest or on the light curing device (10), and the sensor (40) initializes the light curing device (10).

4 Claims, 1 Drawing Sheet

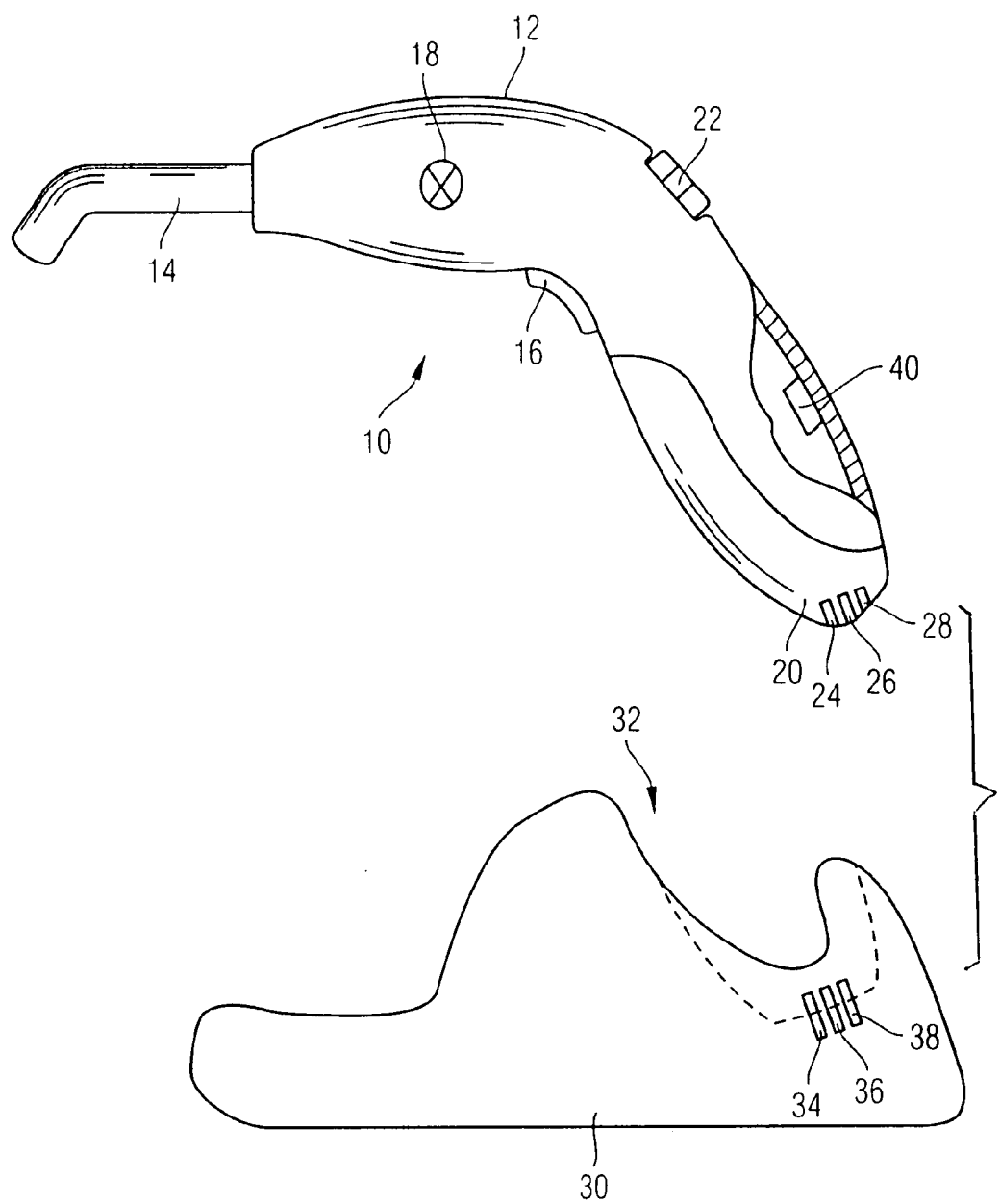

HAND-HELD LIGHT CURING DEVICE

CROSS-REFERENCE TO RELATED APPLICATIONS

This application claims foreign priority benefits under 35 U.S.C. §119(a)-(d) from German patent application ser. no. 10 2006 035 658.6 filed Jul. 31, 2006. In addition, this application claims the benefit under 35 U.S.C. §119(e) of U.S. provisional patent application Ser. No. 60/880,632 filed Jan. 16, 2007.

TECHNICAL FIELD

The invention relates to a hand-held light curing device which may be used by a dental practitioner, and more particularly to light curing device wherein a sensor, which senses the removal of the light curing device from a base station, rest, or docking station, and automatically starts the initialization program of the light curing device.

BACKGROUND OF THE INVENTION

DE-U 8219 588 discloses a light curing device which has a proximity switch. The proximity switch comprises an infrared light source and an infrared detector. When a tooth replacement part is brought into the exposure range of the polymerization light source, which is formed as a halogen lamp, the infrared detector switches the halogen lamp on by means of a switch that is not represented, so that the exposure to light begins.

Although this solution has the advantage that no special action is required for the light curing device to be switched on, the light curing device is necessarily switched on when anything comes into the range of the light source, for example even when a user reaches into the exposure range, for example for cleaning purposes. However, frequent switching on and off is detrimental to the service life of halogen light sources. Moreover, the solution presented there is dangerous to a certain extent. If the protective shield provided there is removed for cleaning purposes, it may be that, as a result of the automatic switching-on function, the user is inadvertently dazzled by the highly concentrated beam of the halogen lamp if the halogen lamp is inadvertently switched on.

It has been known for some time to provide light curing devices with program control. As a result, the required exposure time does not have to be estimated, but can be preset in a program-controlled manner. It is also possible to create specific emission programs, for example color changes or intermittent emissions. Such solutions have been known for some time, an example of such a solution that may be cited being the modern Bluephase™ system of the present applicant. The special high-energy light-emitting diodes with a luminance of 1100 mW per cm or even 1600 mW per cm allow the required curing times to be significantly reduced, for example to ten or even five seconds, depending on the polymer that is used.

Such program controlled devices in most cases require an initialization when the voltage supply is switched on, the microprocessor which performs the program control being activated and the menu choice for the desired programs also being provided.

For the initialization, the actuating switch for the light curing device is briefly actuated once when the light curing device is removed from the base station or the rest. The initialization is started by pressing the actuating switch once, and after three to five seconds the light curing-device is ready for light curing.

If the dentist inadvertently does not hit the actuating switch correctly or inadvertently does not press it, initialization does not take place. In this case, the actuating switch would be actuated for the first time at the intended start of the light curing cycle. If the dentist notices this, the curing cycle is delayed unnecessarily, if on the other hand he does not notice it, the desired curing could fail to take place—at least to the extent intended.

In order to ensure signaling that the light curing device is ready, it has been proposed to emit an audible signal when the initialization process is completed. However, such an additional acoustic signal disturbs the desired peace and quiet in the environment of the dental practice and also demands the attention of the dentist, making such a solution fundamentally unsatisfactory.

OBJECTS AND SUMMARY OF THE INVENTION

The present invention is based on the object of providing a light curing device wherein a sensor, which senses the removal of the light curing device from a base station or rest or docking station, automatically starts the initialization program of the light curing device, which is fundamentally suitable for program control but fits in better with the smooth running of a practice, without requiring any special expenditure for creating or operating it.

According to the invention, it is particularly favorable that the light curing device is activated or initialized without the need for additional user intervention, to be precise, immediately when it is lifted up or removed from the rest or base station. This automatic system enables the user to direct his concentration on setting the light curing device, which is important for the optimum curing of the dental restoration part, without requiring any supplementary work such as the additional actuation of an actuating switch for the activation of the light curing device.

For this purpose, a sensor which senses the removal of the light curing device from the base station or the rest, that is to say in practice the docking station, and automatically starts the initialization program is provided according to the invention. The sensor may be formed for example as a proximity sensor which establishes when the rest or the base station on the one hand and the light curing device on the other hand are no longer in spatial proximity. However, it is also possible to provide a simple switch on the light curing device or the rest and perform the desired initialization by means of its actuation when the light curing device is removed.

Such sensors have the advantage of being insensitive to interference, so that when the light curing device is temporarily set down on a treatment table or the like, renewed initialization is not inadvertently performed.

According to the invention, it is particularly favorable that the initialization takes place, as it were, automatically. The dentist—or possibly the dental technician—cannot remove the light curing device from its rest position without the initialization occurring. Inappropriate operation as a result of incorrect actuation of the actuating switch or failure to perform actuation is not possible, since the actuating switch is not required until the actual polymerization cycle is started.

In this connection, dividing the function between the removal sensor on the one hand and the actuating switch on the other hand creates the possibility of already actively switching the actuating switch in advance—that is for example after only two seconds—when a standard program is concerned. Even if the initialization requires four seconds for example, it is possible here for the start signal to be given in advance, the actual light curing with the standard program then only beginning on completion of the initialization program.

It is in any event preferred that the end of the initialization program is indicated by suitable signaling, for example by a green light-emitting diode or a "ready" area on the display or the indicating device of the light curing device, and that the user can then choose the desired polymerization program directly by means of the menu shown.

However, it goes without saying that straightforward time control is also possible instead of this, that is to say the polymerization cycle is only started and ended by actuating the actuating switch. According to the invention, it is particularly favorable if the sensor is fitted in the light curing device. In the case of this solution, it is possible to perform the initialization immediately the sensor indicates that the light curing device has been removed from the docking station.

If the sensor is fitted on or in the docking station, the information concerning the removal must be transmitted to the light curing device when it is removed from the docking station, which may take place for example via a radio link, infrared link or the like.

According to a further, particularly favorable configuration, it is envisaged to use the charging voltage for the rechargeable batteries of the light curing device that is provided by the docking station for sensing whether the light curing device has been removed from the docking station. The charging voltage is typically provided permanently by the docking station. However, the charging of the rechargeable batteries only takes place when the terminal voltage of the rechargeable batteries is below a predetermined value.

When the charging voltage is no longer being applied to the corresponding contact of the light curing device, that is to say the light curing device has been removed, the charging voltage can then be sensed by means of a switching transistor or a similar voltage sensing device suitable for this purpose.

It goes without saying that, in the case of this configuration, care must be taken that a docking station that is disconnected from the power supply and switched off does not inadvertently lead to initialization. This can also take place for example by means of a resistance measurement, which senses when the contacts of the light curing device are not in connection with the corresponding contacts of the docking station.

According to a particularly advantageous configuration of the invention, it is provided that the sensor is fitted on or in the light curing device and initializes the light curing device when it is picked up.

According to a further advantageous configuration of the invention, it is provided that the sensor is fitted on or in the base station or the rest and transmits a signal, in particular a radio signal, to the light curing device when the light curing device is removed from the base station or the rest.

According to a further advantageous configuration of the invention, it is provided that the sensor is detachably fitted and initializes the light curing device when the light curing device is removed from the base station or the rest.

According to a further advantageous configuration of the invention, it is provided that the sensor is formed as a proximity sensor which triggers when the light curing device is removed from the base station or the rest.

According to a further advantageous configuration of the invention, it is provided that the sensor is formed as a vibration sensor which triggers when the light curing device is removed from the base station or the rest.

According to a further advantageous configuration of the invention, it is provided that the sensor is formed as a contact sensor which is activated when the light curing device, the base station or the rest is touched.

According to a further advantageous configuration of the invention, it is provided that the sensor is formed as a magnetic sensor which triggers when the light curing device is removed from the rest or the base station.

According to a further advantageous configuration of the invention, it is provided that the sensor is formed as a proximity sensor, since it triggers when a hand of the user approaches the light curing device.

According to a further advantageous configuration of the invention, it is provided that the sensor is formed as a switch, in particular as a microswitch, which switches and initializes the light curing device when the light curing device is picked up or removed from the base station or the rest.

According to a further advantageous configuration of the invention, it is provided that the initialization of the light curing device introduces an initialization program, by means of which the light curing device is prepared for the switching-on of the light source.

According to a further advantageous configuration of the invention, it is provided that an initialization program of the light curing device lasts between 0.1 of a second and 8 seconds, in particular between 0.3 of a second and 5 seconds, and preferably approximately 0.5 of a second to 1 second.

According to a further advantageous configuration of the invention, it is provided that the light curing device has an actuating switch, which is mechanically or electrically blocked before the initialization program has run.

According to a further advantageous configuration of the invention, it is provided that the sensor is formed as a voltage sensing device which starts the initialization program when the charging voltage for the rechargeable batteries of the light curing device that is provided by the base station and applied to the light curing device is absent.

BRIEF DESCRIPTION OF THE FIGURE

Further advantages, details and features emerge from the following description of an exemplary embodiment of the invention on the basis of the drawing, in which:

The single drawing shows a schematic view of a light curing device in conjunction with a base station.

DETAILED DESCRIPTION

The FIGURE illustrates a light curing device 10, which is constructed substantially in the form of a gun. The light curing device 10 has a housing 12, which carries a light guide 14 at its front end. A light source 18, which is arranged in the light curing device and is schematically indicated, can be switched on by means of an actuating switch 16.

The light curing device 10 also has a rechargeable battery 20, which is arranged in the handle of the gun-shaped housing 12. An indicating device 22, which indicates the operating state of the light curing device 10 and may possibly also have actuating elements such as a touchscreen or the like in order to make specific operation easier, is also clearly visible on the upper side of the housing.

The housing 12 also has at the lower/rear end of the handle a plurality of contacts 24, 26 and 28. The rechargeable battery 20 can be charged via the contacts 24 to 28, which may also be formed with more than three poles. Provided for this purpose is a base station 30, which may also be referred to as a docking station and has a supporting opening 32. The housing 12 can be inserted by the handle into the supporting opening 32. Formed at the lower end of the supporting opening 32 are contacts 34, 36 and 38, which match the contacts 24 to 28 and serve for supplying the voltage to the light curing device 12. In addition, if need be, data can also be transmitted via the contacts 24 to 28 and 34 to 38.

According to the invention, the light curing device 10 also has a sensor 40. The sensor 40 senses when the light curing device is taken out of the supporting opening 32, and consequently the light curing device is removed from the base station 30.

The sensor immediately switches on an initialization program for the light curing device, which supplies the microprocessor provided in the light curing device 10 with voltage from the rechargeable battery 20, and makes the microprocessor perform the initialization. In the case of the example, the initialization program lasts for three seconds, and it is signaled by means of the indicating device 22 when the light curing device 10 is ready for light curing.

As soon as it is ready, the actuating switch 16 can be actuated, whereas actuation of the actuating switch 16 before it is ready does not result in any light curing taking place.

In the exemplary embodiment represented, the sensor 40 is a proximity sensor which triggers when a hand of the user approaches the light curing device. For example another sensor may use the technique that is used for RFID chips, in that a corresponding RFID scanner is used as the sensor, and an RFID tag or chip is mounted in or on the base station 30. The sensor may be formed as a vibration sensor which triggers when the light curing device is removed from the base station. Alternatively, the sensor 40 may be formed as a magnetic sensor which triggers when the light curing device 10 is removed from the rest or the base station 30.

It goes without saying that any other configuration of the sensor is also possible instead of this. For example, one of the contacts 24, 26 or 28 may take the form of a sensing contact which checks whether there is a connection with the corresponding contact 34, 36 or 38. Furthermore, sensor 40 may also be formed as a microswitch, which for example opens when the light curing device 10 is removed from the base station 30.

The sensor of the light curing device may be formed as a voltage sensing device which starts the initialization program when the charging voltage for the rechargeable batteries of the light curing device 10 that is provided by the base station 30 and applied to the light curing device 10 is absent.

Even if the base station 30 is presented here as a receptacle for the light curing device, it goes without saying that any other stand may be used instead as the base station or rest. For example, it is possible for the dentist to be provided with a stand into which the light curing device is fitted when not in use in the vicinity of the place where treatment is carried out. Such a stand or such a rest typically does not have to have a charging function for the rechargeable battery 20. Nevertheless, here too activation of the sensor 40 when it is removed Is possible, provided that the sensor 40 is formed in such a way that it is activated when it is removed from the stand or the rest.

After the light curing, the light curing device 10 is typically made to revert to the inactive state after a certain waiting time. In this inactive state, the electronics of the light curing device are deenergized, only the sensor 40 being monitored.

If the sensor 40 is formed as a normally open microswitch contact, it is also possible to ensure that it is deenergized to this extent in the inactive state, since, in the set-down state, the light curing device 10 is then completely deenergized on account of the opened microswitch. Only when it is removed from the rest is the microswitch then closed and ensures that the initialization begins.

It goes without saying that the sensor 40 must be of an electronic or mechanical bounce-free configuration. This prevents contact bounce or the like from causing disturbances of the initialization program.

Alternatively it is possible to provide the sensor 40 in the base station 30. Tn the case of this solution, it is required to transmit the switching state of the sensor 40 to the light curing device 10 via suitable means, such as for example a radio link.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. An apparatus comprising:
   a hand-held light curing device having a light source for the dental sector;
   a base station on which the light curing device may be supported when not in use;
   a sensor (40), wherein the sensor senses the removal of the light curing device from the base station, which sensor is fitted on either the base station (30) or on the light curing device (10), the sensor (40) initializing the operation of the light curing device (10) when it senses the removal of the light curing device from the base station,
   an initialization program, and
   an actuating switch (16),
   wherein initialization of the light curing device (10) commences operation of the initialization program, by means of which the light curing device (10) is prepared for the switching-on of the light source (18), the actuating switch (16) being either mechanically or electrically blocked before the initialization program has run.

2. The apparatus as claimed in claim 1, wherein the initialization program of the light curing device (10) lasts between 0.1 of a second and 8 seconds.

3. The apparatus as claimed in claim 1, wherein the sensor (40) is formed as a vibration sensor which triggers when the light curing device (10) is removed from the base station (30).

4. The apparatus as claimed in claim 1, wherein the sensor (40) is fitted on the light curing device (10) and initializes the light curing-device (10) when it is picked up.

* * * * *